United States Patent
Bjerrum et al.

(10) Patent No.: US 6,380,444 B1
(45) Date of Patent: Apr. 30, 2002

(54) PROCESS FOR THE CATALYTIC OXIDATION OF HYDROCARBONS

(75) Inventors: Niels J. Bjerrum, Radhusvej 59 DK-2920, Charlottenlund (DK); Gang Xiao, Bauneporten 21, 2.tv. DK-2800 Lyngby (DK); Hans Aage Hjuler, Dreyersvej 30 DK-2960, Rungsted Kyst (DK)

(73) Assignees: Statoil Research Centre, Trondheim (NO); Niels J. Bjerrum (DK); Gang Xiao (DK); Hans Aage Hjuler (DK)

( * ) Notice: Subject to any disclaimer, the term of this patent is extended or adjusted under 35 U.S.C. 154(b) by 0 days.

(21) Appl. No.: 09/554,068

(22) PCT Filed: Nov. 11, 1998

(86) PCT No.: PCT/DK98/00488

§ 371 Date: Jun. 8, 2000

§ 102(e) Date: Jun. 8, 2000

(87) PCT Pub. No.: WO99/24383

PCT Pub. Date: May 20, 1999

(30) Foreign Application Priority Data

Nov. 12, 1997 (DK) .......................................... 1997 01286

(51) Int. Cl.[7] .......................... C07B 41/02; C07C 27/10
(52) U.S. Cl. ..................................... 568/910.5; 568/910
(58) Field of Search ............................. 568/910, 910.5

(56) References Cited

U.S. PATENT DOCUMENTS

| | | |
|---|---|---|
| 3,979,470 A | 9/1976 | Firnhaber et al. |
| 4,523,040 A | 6/1985 | Olah |
| 4,543,434 A | 9/1985 | Chang |
| 4,804,797 A | 2/1989 | Minet et al. |
| 4,864,073 A | 9/1989 | Han et al. |
| 4,864,074 A | 9/1989 | Han et al. |
| 5,233,113 A * | 8/1993 | Periana et al. .............. 585/500 |

FOREIGN PATENT DOCUMENTS

| | | |
|---|---|---|
| EP | A578384 | 1/1994 |
| WO | A9214738 | 9/1992 |

OTHER PUBLICATIONS

Olah et al., "Superacid–Catalyzed Oxygenation of alkanes", Angew, Chem. Int. Ed., (1978) vol. 17, pp. 909–931.*

Ayusman Sen, Efi Gretz, Thomas F. Oliver and Zhaozhong Jiang, "Palladium (II) Mediated Oxidative Functionalization of Alkanes and Arenes", New J. Chem., 1989, vol. 13, pp. 755–760.

M.N. Vargaftik, I.P. Stolarov, and I.I. Moiseev, "Highly Selective Partial Oxidation of Methane to Methyl Triflouroacetate", J.Chem.Soc., Chem. Commun., 1990, pp. 1049–1050.

Ayusman Sen, "Homogeneous Palladium (II) Mediated Oxidation of Methane Selective Functionalisation Under Mild Conditions", Platinum Metals Rev., 1991, vol. 35, pp. 126–132.

Roy A. Periana, Douglas J. Taube, Eric R. Evitt, Daniel G. Loffler, Paul R. Wentrcek, George Voss, Toshihiko Masuda, "A Mercury–Catalyzed, High–Yield System for the Oxidation of Methane to Menthanol", Science, Jan. 15, 1993, vol. 259, pp. 340–343.

* cited by examiner

Primary Examiner—Samuel Barts
Assistant Examiner—Elvis O. Price
(74) Attorney, Agent, or Firm—Birch, Stewart, Kolasch & Birch, LLP

(57) ABSTRACT

A process for producing an alcohol from a gaseous hydrocarbon, e.g. a lower alkane such as methane, via oxidative reaction of the hydrocarbon in a concentrated sulfuric acid medium in the presence of a catalyst employs an added catalyst comprising a substance selected from iodine, iodine compounds, titanium, titanium compounds, chromiun and chromium compounds.

20 Claims, No Drawings

PROCESS FOR THE CATALYTIC OXIDATION OF HYDROCARBONS

This application is the national phase under 35 U.S.C. §371 of PCT International Application No. PCT/DK98/00488 which has an International filling date of Nov. 11, 1988, which designated the United State of America.

FIELD OF THE INVENTION

The present invention relates to the catalytic oxidation of hydrocarbons to give useful oxidation products thereof. In particular, an important aspect of the invention relates to a process for the production of alkanols, e.g. lower alkanols, such as $C_1$–$C_3$ alkanols (e.g. methanol or ethanol), from the corresponding alkanes (i.e. methane and ethane, respectively, in the case of methanol and ethanol), wherein an alkanol is produced via the formation, and subsequent hydrolysis, of an intermediate (e.g. methyl bisulfate in the case of methane as starting hydrocarbon) formed by catalytic oxidation of the hydrocarbon in a liquid, essentially anhydrous sulfuric acid ($H_2SO_4$) medium containing a catalyst and preferably containing a significant proportion of dissolved sulfur trioxide ($SO_3$).

BACKGROUND OF THE INVENTION

Methane is a raw material of great synthetic importance and an abundant natural resource as the main constituent of natural gas. Nevertheless, it is primarily used only as fuel because two factors limit its use as a raw chemical. The first is that transporting methane gas or even liquefied natural gas is not economical. Therefore, it is highly desirable to transform methane into transportable raw materials or products. The second factor is that methane is a very stable molecule and its direct conversion to useful chemicals is very difficult. Today, over 90% of the produced methane is consumed as heating fuel. Because transportation of natural gas from remote sites is costly, it has often been suggested that natural gas, namely methane, should be converted to more easily transported liquid fuel.

As a raw material for chemical industries, the two leading uses of methane are in the production of methanol and ammonia. Methane must be first transformed into synthesis gas before usage in either ammonia or methanol synthesis. Clearly, this process makes conversion into synthesis gas the dominant process of methane upgrading. The term synthesis gas is generally used for a mixture of carbon monoxide and hydrogen, preferably at a 1:2 or 1:3 ratio. Today the dominant route to the production of synthesis gas is the methane steam reforming process. The reaction can be stoichiometrically expressed as $$CH_4 + H_2O \rightarrow CO + 3H_2$$

A considerable disadvantage of the steam reforming process is that it is an endothermic reaction. The endothermicity results from addition of steam in which a significant amount of energy is required to decompose water into its elements.

In addition to synthesis gas formation, several documents disclose a variety of methods for activating methane to produce other higher molecular weight materials. Mobil Oil Corporation is the assignee in several U.S. patents using sulfur or certain sulfur-containing compounds as the reactants in non-catalytic reactions with methane to produce methyl intermediates which can then be converted to higher molecular weight hydrocarbons.

In U.S. Pat. No. 4,543,434, Chang teaches a process using the following steps:

$$CH_4 + 4S \rightarrow CS_2 + 2H_2S$$

$$CS_2 + 3H_2 (Co \text{ or } Ni) \rightarrow CH_3SH + H_2S$$

$$CH_3SH \ (HZSM\text{-}5) \rightarrow [CH_2] + H_2S$$

$$4H_2S \rightarrow 4H_2 + 4S$$

where "[$CH_2$]" is a hydrocarbon having at least two carbon atoms.

Another Mobil disclosure (U.S. Pat. No. 4,864,073 to Han et al.) suggests a carbonyl sulfide-based process in which methane and carbonyl sulfide are contacted in the presence of ultraviolet light under conditions sufficient to produce $CH_3SH$. No other reaction initiators are said to be present. The reaction scheme is shown to be:

$$CH_4 + COS \rightarrow CH_3SH + CO$$

$$CH_3SH \ (HZSM\text{-}5) \rightarrow [CH_2]H_2S$$

($H_2S \rightarrow S$), a regeneration step $$CO + S \rightarrow COS$$

The selectivity of the first reaction is said to be high, i.e., around 81%, however, the conversion appears to be quite low.

A disclosure similar to that of Chang is found in Mobil's U.S. Pat. No. 4,864,074 to Han et al. As in Chang, the methane is contacted with sulfur. The process conditions are changed, however, so that either $CS_2$ or $CH_3SH$ is formed. These sulfur compounds may then be converted in the presence of the preferred HZSM-5 zeolite catalyst to produce hydrocarbons having two or more carbon atoms. Also, as was the case with "Chang", the step of contacting the methane to produce a methyl-sulfur compound is performed in the absence of a catalyst.

Other methods are known for producing substituted methanes which are suitable for further reaction to heavier hydrocarbons. A thermal methane chlorination process is shown in U.S. Pat. No. 4,804,797 to Minet et al. A similar process is disclosed in U.S. Pat. No. 3,979,470 to Fimhaber et al. (Although a preference for $C_3$ hydrocarbon feeds is expressed in the patent).

One method shown in U.S. Pat. No. 4,523,040 to Olah utilizes either a solid strongly acidic catalyst or a supported Group VIII metal (particularly platinum and palladium) in the gas phase halogenation of methane to produce methyl halides. The patent indicates that monohalides are produced with 85% to 99% selectivity. Olah suggests that subsequent or concurrent catalytic hydrolysis produces methyl alcohol and/or dimethyl ether. Production of methyl oxo-esters is not shown.

The reaction of methane with palladium (II) acetate in trifluoroacetic acid to effect the trifluoroacetoxolation of methane is shown in Sen et al., "Palladium (II) Mediated Oxidative Functionalization of Alkanes and Arenes", *New Journal of Chemistry* (1 989), Vol. 13, No. 10–11, pp. 756–760. A yield of 60% based on palladium was reported when the reaction was practiced using methane as the reactant. Consequently, the reaction with methane utilized palladium as a reactant and not as a catalyst. The extent of methane conversion, selectivity, and reaction rates were not stated.

The Sen et al. article has been criticized in Vargaftik et al., "High Selective Partial Oxidation of Methane to Methyl Trifluoroacetate", *Journal of the Chemical Society, Chemical Communications* (1990), pp. 1049–1050, to the extent that the results were not found to be reproducible. Vargaftik et al. discloses the catalytic oxo-esterification of methane to methyl trifluoroacetate with cobalt in trifluoroacetic acid but shows that palladium is not even suitable for stoichiometric methane oxidation in the process. With Pd, less than 0.1% yield of methyl trifluoroacetate based on palladium (II) trifluoroacetate was obtained.

The Vargaftik et al. article discloses that although palladium is ineffective for the conversion of methane to methyl trifluoroacetate, Co(III) can be used for this reaction. The Co(III) is said to be catalytic in the presence of oxygen. The rate of the reaction was very low, $2.5 \times 10^{-11}$ mol/cc sec, (or four to five orders of magnitude away from typical commercial rates of about $10^{-6}$ mol/cc.sec). Only four turnovers of the Co ion were disclosed. The extent of methane conversion was not stated. In addition to Co, other metals were suggested which were said to allow stoichiometric oxidation of methane to methyl trifluoroacetate in varying yields (based on amount of metal charged): Mn(30%), Cu(0.1%), and Pb(10%).

A later publication by Sen et al ("Homogeneous Palladium (II) Mediated Oxidation of Methane", *Platinum Metals Review*, (1991), Vol 35, No. 3, pp. 126–132) discloses a catalytic system using palladium as the catalyst, peroxytrifluoroacetic acid as the oxidant, and a mixture of trifluoroacetic acid and trifluoroacetic anhydride as the solvent. The reaction rate was low ($4.2 \times 10^{-9}$ mol/cc.sec) and only 5.3 turnovers of Pd were observed. The extent of methane conversion and selectivity were not stated.

There are several lesser routes to upgrade methane such as ammoxidation to HCN, chlorination to chloromethanes, carbon disulfide production and acetylene synthesis. Of great importance is the direct oxidation of methane to produce methanol, formaldehyde, or dimerized products, ethane and ethylene. None of these reactions, however, has yet found large-scale commercial application due to either limited catalytic activity, short catalytic life or low product selectivity. Despite the limited selectivities and yields, numerous studies have been reported on the direct partial or complete oxidation of methane.

A homogeneous system for the selective, catalytic oxidation of methane to methanol via methyl bisulfate was reported (R. A. Periana et al., International Patent Application WO 92/14738). This document describes a novel high-yield system for the catalytic conversion of methane to methanol. Homogeneous reaction takes place in concentrated sulfuric acid and is catalyzed by catalysts comprising metals such as Pd, Tl, Pt, and Au with Hg being most preferred. It is said that they have achieved a yield of 43% at a methane conversion of 50% and 85% selectivity to methyl bisulfate (R. A. Periana et al., *Science*, vol.259, Jan. 15, 1993). The activation of methane is proposed to occur through a net electrophilic displacement reaction with mercuric bisulfate to produce methyl mercuric bisulfate. This species then decomposes to the product and the reduced species, mercurous bisulfate, in the functionalization step. In the redoxidation step, the mercurous bisulfate is oxidized by sulfuric acid, regenerating mercuric bisulfate.The problems associated with this process are that most of the disclosed catalysts are expensive, and the most preferred catalyst, Hg(II), is poisonous and environmentally damaging. Furthermore, the applied gas pressure necessary in order to achieve sufficient methanol yield is very high.

In the present invention we disclose a process which is related to that disclosed in WO 92/14738, but which employs other types of catalysts which are inexpensive, relatively non-poisonous and produces much higher yields of methanol from methane. In addition to this, to achieve the same methanol yield, the required methane gas pressure in the process according to the present invention is much lower than the pressures required in the process described by Periana et al.

DESCRIPTION OF THE INVENTION

In the present invention, initial chemical reaction of a hydrocarbon—in general a hydrocarbon in the gas phase—takes place in a concentrated sulfuric acid ($H_2SO_4$) medium [preferably one containing dissolved sulfur trioxide ($SO_3$), in the present description denoted an $H_2SO_4/SO_3$ medium] and is catalyzed by, in particular, substances containing iodine, titanium or chromium in various oxidation states; more generally, it would appear that species which have a standard reduction potential in the range of 0.5–1.4 volt versus the Standard Hydrogen Electrode are often well suited as catalysts in the context of the present invention.

In the case of alkanes, notably lower alkanes such as those already mentioned above, e.g. methane, an important major product of the reaction in sulfuric acid medium appears to be the corresponding alkyl bisulfate (alkyl hydrogen sulfate), e.g. methyl bisulfate in the case of methane, which may, if so desired, be isolated as an end product per se; such a process constitutes an aspect of the present invention.

Alternatively (and, particularly in the case of methane, importantly), the latter bisulfate product may subjected to a hydrolysis step (e.g. using water or another aqueous medium) to give the corresponding alkanol (alcohol), i.e. methanol in the case of methane.

The reactions of particular interest (illustrated here for methane) are shown below.

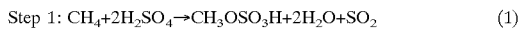

Step 1: $CH_4 + 2H_2SO_4 \rightarrow CH_3OSO_3H + 2H_2O + SO_2$     (1)

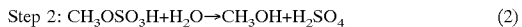

Step 2: $CH_3OSO_3H + H_2O \rightarrow CH_3OH + H_2SO_4$     (2)

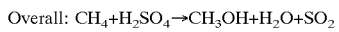

Overall: $CH_4 + H_2SO_4 \rightarrow CH_3OH + H_2O + SO_2$

It is envisaged that in order to reduce consumption of the concentrated sulfuric acid medium in the process, a further step could be incorporated wherein $SO_2$ formed in the process is reoxidized [using, for example, an oxygen-containing gas (such as air or substantially pure oxygen)] to $SO_3$ which would then react with water present in the system to give sulfuric acid. Thus, a step such as the following is contemplated:

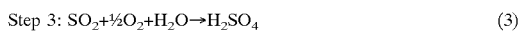

Step 3: $SO_2 + \frac{1}{2}O_2 + H_2O \rightarrow H_2SO_4$     (3)

With incorporation of such a step in a process of the invention, the overall reaction of particular interest could then be written as:

Overall: $CH_4 + \frac{1}{2}O_2 \rightarrow CH_3OH$     (4)

The concentrated essentially 100% sulfuric acid used as the reaction medium in the initial stage of the process plays several roles. Firstly, it is a strong acid exerting a super-acidic function in the system which contributes to retention, absorption and/or binding of the hydrocarbon in the medium during the oxidative reaction in question. Secondly, sulfuric acid acts as an oxidant, being itself reduced to sulfur dioxide. Further, it functions as a reactant in its own right, combining e.g. with alkanes such as methane to initially form a sulfate ester species, and as a solvent for the hydrocarbon and the reaction products thereof.

Thus, as already indicated to some extent, an important aspect of the present invention relates to a process for producing an alcohol from a gaseous hydrocarbon—such as the production of an alkanol from a corresponding alkane, especially methanol from methane—via oxidative reaction of the hydrocarbon in a concentrated sulfuric acid medium in the presence of a catalyst, wherein the substance added as catalyst comprises a substance selected from the group consisting of iodine, iodine compounds, titanium, titanium compounds, chromium and chromium compounds. In preferred variants of the process, the latter reaction takes place in a pressurizable reaction vessel. Stirring or other effective mixing of the reaction medium during the reaction is generally to be preferred.

In order to form the desired alcohol (e.g. alkanol) from the product or products of the reaction of the hydrocarbon in the sulfuric acid medium, the product or products (e.g. an alkyl bisulfate and/or dialkyl sulfate) in question is/are suitably subjected to an hydrolysis step, e.g. using water or an aqueous medium.

The sulfuric acid medium employed in the process preferably contains dissolved $SO_3$ in an amount of from 0% by weight up to the solubility limit of $SO_3$ in $H_2SO_4$ under the particular reaction conditions (temperature, pressure, etc.) employed. The $SO_3$ content of the medium will, however, generally be in the range of 0–65% by weight (% w/w), and normally in the range of 30–65% w/w.

The reaction temperature in the sulfuric acid medium will normally preferably be in the range of 20–400° C., often around 200° C. With respect to pressure conditions, particularly when the gas-phase hydrocarbon in question is an lower alkane, e.g. methane, the reaction in the sulfuric acid medium will preferably take place in a pressurizable reaction vessel into which the hydrocarbon is introduced to an initial pressure in the range of 1–500 bar. It is, however, generally preferable to employ a initial pressure in the range of 20–80 bar, such as in the range of 40–70 bar.

With regard to catalytic substances of interest in relation to the present invention, the added catalyst employed is preferably one comprising:

iodine (elemental iodine) or a compound of iodine in any oxidation state (e.g. −1 or +5);

titanium (metal, e.g. in powder form) or a compound of titanium in any oxidation state (e.g. +3 or +4), such as titanium(IV) oxide (i.e. titanium dioxide); or chromium (metal, e.g. in powder form) or a compound of chromium in any oxidation state (e.g. +2, +3 or +6), such as a chromium (VI) compound in the form of, e.g., a chromate or dichromate (e.g. of an alkali metal such as sodium or potassium).

Among catalytic substances of the latter types, particularly suitable substances are believed to include those having a standard reduction potential in the range of 0.5–1.4 volt versus the Standard Hydrogen Electrode (SHE).

The invention thus provides, inter alia, catalytic systems in a pressurized reactor vessel, comprising a catalyst such as a compound containing iodine, titanium or chromium, an active reaction medium comprising liquid $H_2SO_4/SO_3$, and a gaseous hydrocarbon as reactant. As already indicated, the resulting liquid containing oxo-esters (sulfate esters) may be hydrolyzed to produce alcohols or used to produce other compounds. The preferred parameters (temperature, pressure, $SO_3$ content, added catalysts etc.) for such catalytic systems are those already mentioned above in the context of processes of the invention.

EXAMPLES

The following examples are batch processes intended to illustrate parts of the overall inventive process, in particular the alkyl esterification reaction utilizing methane as the reactant. The remainder of the process steps are easily selectable from known processes. Continuous processes are also feasible.

A. A 200 ml pressure reactor was charged with 25 ml of fuming $H_2SO_4$ (65% $SO_3$) and 0.00674 mol of $KIO_3$. The reactor was flushed with methane and heated to 200° C. under 42 Bar of methane. The content of the reactor was stirred. After one hr the reactor was cooled to 25° C. A gas sample of the gas in the reactor was obtained for gas chromatographic analysis. An aliquot of the reaction mixture was first diluted with 19 volumes of water and the resulting solution heated in a sealed container for 4 hours. The resulting solution was quantitatively analyzed for the free $CH_3OH$ by high pressure liquid chromatography (HPLC) using a Nucleosil C18 column and a refractive index detector. Based on the HPLC measurements, the yield of methanol was 36% (Table I, entry 4). Gas chromatographic analysis showed that fairly large amount of $SO_2$ and trace levels of $CO_2$ were produced. The amount of produced methanol is several orders of magnitude higher than the $KIO_3$.

B. To show the effect of $KIO_3$ concentration, the general procedure of Example A was repeated with 0.00169 mol and 0.01011 mol of $KIO_3$ for two hours under 42 Bar of methane. The results given in Table I (entries 1–3) show that 0.00169 mol of $KIO_3$ gives the highest yield of methanol.

C. To show the greater effectiveness of $KIO_3$ as compared to Hg(II), the general procedure of Example A was repeated using 0.00674 mol of $KIO_3$ and 0.00674 mol of $HgSO_4$ as the catalysts, respectively. The results shown in Table I show that both in the case of 25 ml acid (entries 4 and 5) and 50 ml acid (entries 6 and 7) $KIO_3$ gives better yields of methanol compared to $HgSO_4$.

D. As a "blank run", the procedure of Example A was repeated but without added catalyst. As may be seen from the results in Table I (entry 8) no methanol was produced in the reaction.

E. To show the effect of acid concentration, the general procedure of Example A was repeated with 100% $H_2SO_4$ and fuming $H_2SO_4$ (32.5% $SO_3$), 0.00674 mol $KIO_3$, and 42 Bar of methane for one hour. The results shown in Table I (entries 9 and 10) show that the yield of methanol was much higher in the case of higher acid concentration.

F. To show the effect of different acid amount, the general procedure of Example A was repeated with 25 ml, 50 ml and 75 ml of fuming $H_2SO_4$ (65% $SO_3$) and $KIO_3$ as the catalyst. The best methanol yield was found with 50 ml acid and two hours of reaction time (84%), and with 75 ml acid and one hour of reaction time (80%) (entries 11 and 12). The same experiments were done using $HgSO_4$ as the catalyst. The yields of methanol were lower compared with $KIO_3$ (entries 7 and 5).

G. To show the effect of temperature, the general procedure of Example A was repeated at 100° C., 120° C., 140° C., 160° C., 180° C., 190° C., 200° C., 210° C. and 220° C. with 0.00674 mol $KIO_3$ for one hour under 42 Bar of methane. The results shown in Table I (entries 13–20) show that increasing temperatures from 100° C.–210° C. lead to increased yields of methanol. At 220° C., a loss in yield was observed.

H. To show the effect of reaction time, the general procedure of Example A was repeated with reaction time of 20 min., 40 min., 60 min., and 120 min. using $KIO_3$ as the catalyst. The results show that increasing reaction time lead to increased yields of methanol. However, 60 min. is perhaps the optimal duration considering the energy cost (entries 21, 22, 4 and 1).

since $TiO_2$ is dissolved in the strong acid) works as a catalyst and gives methanol yields of 71% and 49%, respectively (entries 28 and 29).

M. To show that the reaction also proceeds with compounds containing chromium, the general procedure A was repeated with $K_2Cr_2O_7$ as the catalyst with 50 ml of fuming $H_2SO_4$ (65% $SO_3$) for two hours. The result shows that chromium in oxidation VI (and III since part of the chromium must be reduced) works as a catalyst and gives a methanol yield of 30% (entry 30).

TABLE I

| Entry | Catalyst | Catalyst Amount (mol) | Acid | Temp (° C.) | Duration (min.) | Yield (%) |
|---|---|---|---|---|---|---|
| 1 | $KIO_3$ | 0.00674 | 25 ml $H_2SO_4$(65% $SO_3$) | 200 | 120 | 37 |
| 2 | $KIO_3$ | 0.00169 | 25 ml $H_2SO_4$(65% $SO_3$) | 200 | 120 | 41 |
| 3 | $KIO_3$ | 0.01011 | 25 ml $H_2SO_4$(65% $SO_3$) | 200 | 120 | 35 |
| 4 | $KIO_3$ | 0.00674 | 25 ml $H_2SO_4$(65% $SO_3$) | 200 | 60 | 36 |
| 5 | $HgSO_4$ | 0.00674 | 25 ml $H_2SO_4$(65% $SO_3$) | 200 | 60 | 24 |
| 6 | $KIO_3$ | 0.00674 | 50 ml $H_2SO_4$(65% $SO_3$) | 200 | 60 | 50 |
| 7 | $HgSO_4$ | 0.00674 | 50 ml $H_2SO_4$(65% $SO_3$) | 200 | 60 | 41 |
| 8 | None | — | 25 ml $H_2SO_4$(65% $SO_3$) | 200 | 60 | 0 |
| 9 | $KIO_3$ | 0.00674 | 25 ml 100% $H_2SO_4$ | 200 | 60 | 6 |
| 10 | $KIO_3$ | 0.00674 | 25 ml $H_2SO_4$(32.5% $SO_3$) | 200 | 60 | 13 |
| 11 | $KIO_3$ | 0.00674 | 50 ml $H_2SO_4$(65% $SO_3$) | 200 | 120 | 84 |
| 12 | $KIO_3$ | 0.01348 | 75 ml $H_2SO_4$(65% $SO_3$) | 200 | 60 | 80 |
| 13 | $KIO_3$ | 0.00674 | 25 ml $H_2SO_4$(65% $SO_3$) | 100 | 60 | 1 |
| 14 | $KIO_3$ | 0.00674 | 25 ml $H_2SO_4$(65% $SO_3$) | 120 | 60 | 9 |
| 15 | $KIO_3$ | 0.00674 | 25 ml $H_2SO_4$(65% $SO_3$) | 140 | 60 | 18 |
| 16 | $KIO_3$ | 0.00674 | 25 ml $H_2SO_4$(65% $SO_3$) | 160 | 60 | 20 |
| 17 | $KIO_3$ | 0.00674 | 25 ml $H_2SO_4$(65% $SO_3$) | 180 | 60 | 27 |
| 18 | $KIO_3$ | 0.00674 | 25 ml $H_2SO_4$(65% $SO_3$) | 190 | 60 | 30 |
| 19 | $KIO_3$ | 0.00674 | 25 ml $H_2SO_4$(65% $SO_3$) | 210 | 60 | 31 |
| 20 | $KIO_3$ | 0.00674 | 25 ml $H_2SO_4$(65% $SO_3$) | 220 | 60 | 29 |
| 21 | $KIO_3$ | 0.00674 | 25 ml $H_2SO_4$(65% $SO_3$) | 200 | 20 | 31 |
| 22 | $KIO_3$ | 0.00674 | 25 ml $H_2SO_4$(65% $SO_3$) | 200 | 40 | 35 |
| 23 | KI | 0.00674 | 25 ml $H_2SO_4$(65% $SO_3$) | 200 | 20 | 26 |
| 24 | $I_2$ | 0.00674 | 25 ml $H_2SO_4$(65% $SO_3$) | 200 | 60 | 74 |
| 25 | $I_2$ | 0.00674 | 50 ml $H_2SO_4$(65% $SO_3$) | 200 | 60 | 50 |
| 26 | $CH_3I$ | 0.00674 | 25 ml $H_2SO_4$(65% $SO_3$) | 200 | 60 | 73 |
| 27 | $CH_3I$ | 0.00674 | 50 ml $H_2SO_4$(65% $SO_3$) | 200 | 60 | 57 |
| 28 | $TiO_2$ | 0.00674 | 25 ml $H_2SO_4$(65% $SO_3$) | 200 | 60 | 71 |
| 29 | $TiO_2$ | 0.00674 | 50 ml $H_2SO_4$(65% $SO_3$) | 200 | 120 | 49 |
| 30 | $K_2Cr_2O_7$ | 0.00674 | 50 ml $H_2SO_4$(65% $SO_3$) | 200 | 120 | 30 |

Note: All experiments were carried out at a methane pressure of 42 bar.

I. To show how the reaction proceeds with different forms of iodine, the general procedure A was repeated with KI as the catalyst at 200° C. for 20 min. The result shows that $I^{-1}$ also works as a catalyst (entry 23).

J. To show that the reaction also proceeds with elementary $I_2$, the general procedure A was repeated with $I_2$ as the catalyst with 25 ml and 50 ml of fuming $H_2SO_4$ (65% $SO_3$), respectively. The results show that $I_2$ works as a catalyst and gives methanol yields of 74% and 50%, respectively (entries 24 and 25).

K. To show that the reaction also proceeds with organic compounds containing iodine, the general procedure A was repeated with $CH_3I$ as the catalyst with 25 ml and 50 ml of fuming $H_2SO_4$ (65% $SO_3$), respectively. The results show that $CH_3I$ works as a catalyst and gives methanol yields of 73% and 57%, respectively (entries 26 and 27).

L. To show that the reaction also proceeds with titanium compounds, the general procedure A was repeated with $TiO_2$ as the catalyst with 25 ml (1 hr) and 50 ml (2 hrs) of fuming $H_2SO_4$ (65% $SO_3$), respectively. The results show that $TiO_2$ (and Ti(IV) and Ti(III) compounds The above examples are merely illustrative and are not to be interpreted as limiting the scope of the disclosed invention in any manner.

Moreover, it should be clear that one of ordinary skill in this art could envisage equivalents to the processes described in the accompanying claims, and that such equivalents would be within the scope and spirit of the claimed invention.

What is claimed is:

1. A process for producing an alcohol from a gaseous hydrocarbon via oxidative reaction of said hydrocarbon in a concentrated sulfuric acid medium in the presence of a catalyst, wherein the substance added as catalyst comprises a substance selected from the group consisting of iodine, iodine compounds, titanium, titanium compounds, chromium and chromium compounds.

2. A process according to claim 1, wherein said reaction takes place in a pressurizable reaction vessel.

3. A process according to claim 1, wherein said sulfuric acid medium is stirred during said reaction.

4. A process according to claim 1, wherein the product or products of said reaction of said hydrocarbon is/are subjected to a hydrolysis step.

5. A process according to claim 1, wherein said hydrocarbon is an alkane, and said alcohol is an alkanol.

6. A process according to claim 5, wherein said alkane is methane, and said alcohol is methanol.

7. A process according to claim 1, wherein said sulfuric acid medium contains dissolved $SO_3$ in an amount of from 0% by weight up to the solubility limit of $SO_3$ in $H_2SO_4$ under the reaction conditions in question.

8. A process according to claim 7, wherein said sulfuric acid medium contains 0–65% w/w of dissolved $SO_3$.

9. A process according to claim 1, wherein the reaction temperture in said sulfuric acid medium is in the range of about 20 to about 400° C.

10. A process according to claim 9, wherein the reaction temperature in said sulfuric acid medium is about 200° C.

11. A process according to claim 1, wherein said hydrocarbon is gaseous methane, and said reaction in said sulfuric acid medium takes place in a pressurizable reaction vessel under an initial gas pressure in the range of about 1 to about 500 bar.

12. A process according to claim 11, wherein said reaction in said sulfuric acid medium takes place in a pressurizable reaction vessel under an initial gas pressure in the range of about 20 to about 80 bar.

13. A process according to claim 1, wherein said added catalyst comprises titanium or a compound of titanium in any oxidation state.

14. A process according to claim 13, wherein said added catalyst is titanium dioxide.

15. A process according to claim 1, wherein said catalyst comprises chromium or a compound of chromium in any oxidation state.

16. A process according to claim 15, wherein said catalyst comprises a chromium (VI) compound.

17. A process according to claim 16, wherein said catalyst comprises a chromate or dichromate of an alkali metal.

18. A process according to claim 1, wherein said catalyst has a standard reduction potential in the range of about 0.5 to about 1.4 volt versus the Standard Hydrogen Electrode.

19. A process for producing an alcohol from a gaseous hydrocarbon via an oxidative reaction of said hydrocarbon in a concentrated sulfuric acid medium in the presence of a catalyst, wherein catalyst comprises elemental iodine or a compound of iodine in any oxidation state.

20. A process for producing an alcohol from a gaseosus hydrocarbon via oxidative reaction of said hydrocarbon in a concentrated sulfuric acid medium in the presence of a catalystic, wherein the catalyst comprises elemental iodine.

* * * * *